United States Patent [19]

McNally et al.

[11] Patent Number: 5,593,696
[45] Date of Patent: Jan. 14, 1997

[54] STABILIZED COMPOSITION OF FAMOTIDINE AND SUCRALFATE FOR TREATMENT OF GASTROINTESTINAL DISORDERS

[75] Inventors: Gerard P. McNally, Strafford; Edward J. Roche, Paoli, both of Pa.

[73] Assignee: McNeil-ppc, Inc., Milltown, N.J.

[21] Appl. No.: 342,775

[22] Filed: Nov. 21, 1994

[51] Int. Cl.$^6$ ........................................ A61K 9/24
[52] U.S. Cl. .................... 424/472; 424/464; 424/470
[58] Field of Search .................... 424/464, 473, 424/467; 514/12

[56] References Cited

U.S. PATENT DOCUMENTS

| | | | |
|---|---|---|---|
| 3,048,526 | 8/1962 | Boswell | 167/82 |
| 3,922,338 | 11/1975 | Estevenel et al. | 424/21 |
| 4,283,408 | 8/1981 | Hirata et al. | 424/270 |
| 4,915,954 | 4/1990 | Ayer et al. | 424/473 |
| 5,175,147 | 12/1992 | Folkman et al. | 514/12 |
| 5,213,807 | 5/1993 | Chemburkar et al. | 424/472 |
| 5,213,808 | 5/1993 | Bar-Shalom et al. | 424/473 |
| 5,229,131 | 7/1993 | Amidon et al. | 424/451 |
| 5,229,137 | 7/1993 | Wolfe | 424/687 |
| 5,260,072 | 11/1993 | Roche et al. | 424/464 |

FOREIGN PATENT DOCUMENTS

| | | |
|---|---|---|
| 0286781 | 10/1988 | European Pat. Off. . |
| 0294933 | 12/1988 | European Pat. Off. . |
| WO92/09286 | 6/1992 | WIPO . |

*Primary Examiner*—Thurman K. Page
*Assistant Examiner*—William E. Benston, Jr.
*Attorney, Agent, or Firm*—Connolly & Hutz

[57] ABSTRACT

Oral dosage forms are disclosed which are effective for treating of gastric disorders. The dosage forms contain, as active ingredients, famotidine and sucralfate. In the dosage form, the famotidine is provided with a barrier layer which prevents interaction between the famotidine and the sucralfate, which improves the stability of the dosage form.

18 Claims, No Drawings

STABILIZED COMPOSITION OF FAMOTIDINE AND SUCRALFATE FOR TREATMENT OF GASTROINTESTINAL DISORDERS

FIELD OF THE INVENTION

The invention relates to compositions for treating gastrointestinal disorders and distress which contain a combination of active ingredients and to solid dosage forms of such compositions.

BACKGROUND AND PRIOR ART

It is known that certain histamine $H_2$-receptor antagonists are effective in treating gastric disorders such as peptic and gastric ulcers. Familiar compounds of this type are cimetidine, ranitidine and famotidine.

The compound 3-[[[2-[(aminoiminomethyl)amino]-4-thiazolyl]methtyl]thio]-N-(aminosulfonyl)propanimidamide ("famotidine") is an effective anti-ulcerative of this class.

Sucralfate is a complex of sulfated sucrose and aluminum hydroxide which acts as an anti-ulcerative by forming a cytoprotective barrier at the ulcer site. The drug is administered orally, and has been found useful in treatment of gastric and duodenal ulcers. See, W. A. Ritschel, Antacids and Other Drugs in GI Diseases, Drug Intelligence Publications: Hamilton, Ill. (1984).

It has been proposed to administer sucralfate in combination with histamine $H_2$-receptor antagonists. For example, published application WO 92/09286 discloses pharmaceutical compositions which contain a histamine $H_2$-receptor antagonist (such as famotidine) in combination with sucralfate, in which compositions the sucralfate acts as a bioadhesive and buffer. It is disclosed that the histamine $H_2$-receptor antagonist and the sucralfate form a bioadhesive complex in vivo, which targets the antagonist to the stomach wall. The disclosed compositions may be prepared in the form of powders, tablets or liquid suspensions.

When famotidine and sucralfate are administered together, the sucralfate acts to neutralize stomach acidity while famotidine acts to inhibit acid secretion, and the combined action is very effective.

While compositions containing famotidine and sucralfate are quite effective in treating gastric disorders, it has been found that, in compositions which contain both famotidine and sucralfate in combination, the sucralfate tends to degrade the famotidine, making the compositions less efficacious.

SUMMARY OF THE INVENTION

The object of the invention is to improve the stability of pharmaceutical compositions which comprise a combination of famotidine and sucralfate by preventing degradation of the famotidine component of the composition.

In accordance with the invention, a pharmaceutical composition is provided which contains, as the primary active ingredients, famotidine and sucralfate in amounts effective to alleviate symptoms of gastric distress. The famotidine is present in the composition in particulate (granulate) form, and the particulate famotidine is provided with a protective barrier layer sufficient to prevent interaction between the famotidine and the sucralfate present in the composition. The barrier layer is preferably a polymeric coat which dissolves partially in vivo in the stomach environs to release the coated famotidine. It has been found that combinations of coated famotidine with sucralfate are significantly more stable than combinations of uncoated famotidine with sucralfate.

DESCRIPTION OF THE PREFERRED EMBODIMENTS

Both sucralfate and famotidine are commercially available in the form of powders suitable for encapsulation and the like. The compound famotidine and it preparation is described, for example, in U.S. Pat. No. 4,283,408.

The famotidine and sucralfate components of the invention are provided in combination in a solid dosage form. In accordance with the invention, interaction between the famotidine and the sucralfate is prevented by providing the famotidine within a protective barrier layer which prevents interaction between the famotidine and the sucralfate. Preferably the barrier layer is a polymer coating which substantially encapsulates each discrete granule containing famotidine. The famotidine thus encapsulated is then combined with sucralfate to form a solid dosage form.

The barrier polymer is preferably composed of a pharmaceutically acceptable film-forming polymer which is physiologically inert, degradable in vivo, and prevents the therapeutic ingredients in the separate portions of the solid dosage form from contacting. Suitable pharmaceutically acceptable polymers may be selected from cellulose derivatives, polyvinyl pyrrolidone (containing little or no polymerization initiator), polyvinyl alcohol, polyvinyl acetate, polyethylene glycols, copolymers of styrene and acrylate, copolymers of acrylic acid and methacrylic acid, copolymers of methacrylic acid and ethylacrylate, copolymers of methyl methacrylate and methacrylate, copolymers of acrylic acid and tertiary amino alkyl methacrylate, copolymers of methacrylate and tertiary amino alkyl methacrylate, copolymers of ethylacrylate methyl methacrylate and quaternary-amino alkyl methacrylate and combinations of two or more thereof. Cellulose derivatives include pharmaceutically-acceptable cellulose derivatives selected from the group consisting of methyl cellulose, hydroxypropyl methylcellulose, ethyl cellulose, hydroxyethyl cellulose, hydroxypropyl cellulose, carboxymethyl cellulose, cellulose acetate butyrate, cellulose acetate phthalate, hydroxypropyl methylcellulose phthalate, hydroxypropyl methylcellulose acetate succinate and combinations of two or more thereof. The acrylic acid and methacrylic acid copolymers listed above also includes copolymers of sodium and potassium salts thereof. A suitable ester copolymer of methacrylic and tertiary amino alkyl methacrylate is dimethylaminoethyl methacrylate.

The famotidine-containing granules may be coated by any conventional coating process, such as roto-coating (coating in a rotogranulator), Wurster coating or fluid bed particle coating.

Examples of suitable coatings are shown in the following table:

| Polymer System | Coat Level | Polymer Ratio |
| --- | --- | --- |
| Cellulose Acetate/PVP | 8–18% | 90/10 to 60/40 |
| Cellulose Acetate Butyrate/PVP | 8–18% | 90/10 to 60/40 |
| Cellulose Acetate/HPC | 8–18% | 90/10 to 50/50 |
| Cellulose Acetate Butyrate/HPC | 8–18% | 90/10 to 50/50 |
| Cellulose Acetate/ methacrylic acid copolymers | 8–18% | All ratios |

| Polymer System | Coat Level | Polymer Ratio |
|---|---|---|
| (Eudragit E 100) | | |
| Cellulose Acetate Butyrate/ Eudragit E 100 | 8–18% | All ratios |
| Ethyl Cellulose/PVP | 8–18% | 90/10 to 60/40 |
| Ethyl Cellulose/HPC | 8–18% | 90/10 to 50/50 |
| Ethyl Cellulose/Eudragit E 100 | 8–18% | All ratios |
| HPC | 10–20% | NA |
| HEC | 10–20% | NA |
| Eudragit E 100 | 10–20% | NA |
| HPMC | 10–20% | NA |
| HEC/HPMC | 10–20% | All ratios |
| HPC/HPMC | 10–20% | All ratios |
| HEC/HPC | 10–20% | All ratios |
| VPS | 10–20% | NA |
| CA/2-VPS | 8–18% | All ratios |
| CAB/2-VPS | 8–18% | All ratios |
| Ethyl Cellulose/2-VPS | 8–18% | All ratios |
| Cellulose Triacetate/PVP | 8–18% | 90/10 to 60/40 |
| Cellulose Triacetate/HPC | 8–18% | 90/10 to 50/50 |
| Cellulose Triacetate/ Eudragit E 100 | 8–18% | All ratios |

PVP — polyvinylpyrrolidone
HPC — Hydroxypropyl cellulose
HEC — Hydroxyethyl cellulose
HPMC — Hydroxypropylmethyl cellulose
CA — Cellulose Acetate
CAB — Cellulose Acetate Butyrate
Eudragit E 100 — Methylacrylic acid copolymers
VPS — 2-vinyl pyridine styrene copolymer The preferred coatings are cellulose acetate, cellulose triacetate and cellulose acetate butyrate with polyvinyl pyrrolidone, methylaminoethyl-methacrylate and neutral methacrylic acid esters (Eudragit E-100), copolymers of 2-vinylpyridine and styrene and hydroxypropylcellulose. Particularly preferred grades of polymers are cellulose acetate 320-S, 398-10,437-75S; cellulose acetate butyrate 171, 381 and 500 (both of cellulose acetate and cellulose acetate butyrate are available from FMC and fully described in *Cellulose Esters: Polymers for Drug Delivery* published in 1986; Povidone K29/32 and K90 (which is fully described in the USP); Klucel EF, LF, and JF (HPC having average molecular weight of from about 60,000 to about 125,000); Methocel E5 and E15; Natrosol 250L; and Ethocel N10. The amount of coating applied as a weight percentage of the weight of the coated granules will vary with the coating process. The appropriate amount of coating can be determined by determining the dissolution of the active pharmaceutical suitable for the treatment of gastric disorders with various coating thicknesses following the dissolution tests set forth in *The United States Pharmacopeia XXII*. As a general rule, the amount of coating will vary from about 8% to about 20% based on the weight of the coated granule. In one preferred embodiment of the present invention granules formed by a wet rotogranulation process would be rotocoated with from about 8% to about 18% weight percent of a polymer blend of cellulose acetate and methylaminoethyl-methacrylate and neutral methacrylic acid ester.

The protected famotidine component and the sucralfate component are then combined in desired amounts to provide a solid dosage form. Preferably, the solid dosage form comprises a tablet, optionally a chewable tablet, or a capsule encasing the materials. Methods for manufacturing solid dosage forms are known in the art. Reference is made to Remingtons Pharmaceutical Sciences, 18th edition, Mack Publishing Company, and to Pharmaceutical Dosage Forms: Tablets, Vols. 1–3, 2d edition, Marcel Dekker.

As an alternate embodiment, the dosage form of the invention may comprise a bilayer tablet having one layer of famotidine and one layer of sucralfate, the layers being separated by a protective layer composed of one of the above-described barrier materials. Means of preparing bilayer tablets are well known and are not described in detail. Other active ingredients, such as additional antacids, may optionally be incorporated into the compositions.

Any of a variety of excipients or non-active agents are suitable for use in the solid dosage forms. Excipients include fillers, binders, sweeteners (natural or artificial), lubricants, glidants, disintegrants, colors, adsorbents, acidifying agents and flavoring agents. The choice of excipient will depend on the solid oral dosage form desired (i.e. tablets, pills or capsule) and whether the dosage is to be chewable or swallowable. The following non-limiting list of excipients provides illustrative excipients that could be used in a chewable solid oral dosage form:

a) an effective amount of a sweetener selected from the group consisting of mannitol, dextrose, fructose, sorbitol, sucrose and lactose;

b) an effective amount of a binder selected from the group consisting of microcrystalline cellulose, alginic acid, acacia acid, carboxymethyl cellulose and hydroxypropyl cellulose;

c) an effective amount of an artificial sweetener selected from the group consisting of aspartame, sucralose and saccharin;

d) an effective amount of a lubricant selected from the group consisting of magnesium stearate, talc, stearic acid, calcium stearate, zinc stearate, stearic acid, hydrogenated vegetable oil, leucine, glycerides, and sodium stearyl fumarate; and e) an effective amount of an acidifying agent selected from the group consisting of citric acid and malic acid;

f) an effective amount of flavoring agent selected from the group consisting of artificial and natural flavors; and g) an effective amount of a filler selected from the group consisting of dibasic calcium phosphate dihydrate and monobasic calcium phosphate monohydrate.

Additionally, the components listed above (without the sweeteners and flavorants) could be used in swallowable tablets or caplets. For the formulation of swallowable caplets or tablets it may be desirable to incorporate an effective amount of a disintegrant such as disintegrants selected from the group consisting of carboxymethyl cellulose, alkali salts of carboxymethyl cellulose (such as a sodium salt), sodium cellulose glycolate, sodium carmellose glycolate, sodium carboxymethyl starch, sodium starch glycolate, and crosscarmellose sodium.

The amounts of famotidine and sucralfate present in the composition are such as to effect relief of symptoms of gastric disorders or distress. The dosage of famotidine present in each solid dosage form is preferably 5–50 mg, measured either as coated or uncoated famotidine. The sucralfate is preferably present in excess in relation to the famotidine. The currently preferred ratio by weight of famotidine (calculated as famotidine including barrier layer) is from about 1:75 to about 1:10. A typical dosage form contains 10mg famotidine and 500 mg sucralfate.

Preparation of the compositions of the invention and examination of the stability properties of the compositions are set forth in the following example, which is provided as illustration and not as limitation.

EXAMPLES 1–4 AND A–D

In these examples, the stability properties of combined famotidine and sucralfate compositions are reported. In the comparison compositions (A-D), the famotidine component is not protected from interaction with the sucralfate component. In the compositions prepared according to the invention (1-4), the famotidine is encapsulated within a protective barrier coating prior to being combined with sucralfate.

Tablet forms were prepared on a Carver press which contained 10 mg of famotidine (coated or uncoated) and 500mg of sucralfate, free of excipients. In examples 1-4 (according to the invention), the particulate famotidine was coated with a polymer blend of hydroxypropylcellulose and cellulose acetate prior to admixture with sucralfate and tabletting. Samples 1, 2, A and B were prepared as bilayer tablets, while samples 3, 4, C and D were prepared as single layer tablets by pressing blends of famotidine and sucralfate. All sample were prepared in duplicate and the results shown in Table 1 represent the mean values obtained from two samples.

All tablets were subjected to an accelerated stability test comprising storing the tablets for 5 weeks in an open dish at 40 degrees C. and 75% relative humidity. Degradates were detected by HPLC. See generally, Beaulieu et al., J. of Pharm. and Biomed. Analysis 7:1705 (1989).

TABLE 1

| SAMPLE | ASSAY (mg/Tab) | | DEGRADATES | | | | TOTAL |
|---|---|---|---|---|---|---|---|
| | Initial | 5 weeks | % A6 | % A2 | % A1 | % A3 | Degradates |
| 1 | 10.2 | 9.6 | 0.09 | 0.09 | 0.46 | 0.09 | 0.72 |
| 2 | 7.3 | 11.0 | 0.31 | 0.31 | 1.64 | 0.23 | 2.50 |
| A | 11.0 | 8.5 | 0.08 | 0.08 | 0.43 | 0.07 | 0.66 |
| B | 11.3 | 7.0 | 0.08 | 0.08 | 0.51 | 0.07 | 0.74 |
| 3 | 10.3 | 10.8 | 0.02 | 0.02 | 0.11 | 0.03 | 0.19 |
| 4 | 10.3 | 9.8 | 0.03 | 0.03 | 0.17 | 0.05 | 0.28 |
| C | 24.5 | 12.9 | 1.84 | 1.84 | 8.18 | 0.88 | 12.73 |
| D | 9.9 | 18.0 | 1.89 | 1.89 | 8.63 | 0.92 | 13.34 |
| Degradate Limits: | | | 1.00 | 0.50 | 0.50 | 0.50 | 2.50 |

A1 = 3-[(2-Guanidinithiazole-4-yl)methylthio]propionyl sulphamide
A2 = 3-[[[2-[(Diaminomethylene)amino]-4-thiazolyl]methyl]thio]propionic acid
A3 = 3-[[[2-[(Diaminomethylene)amino]-4-thiazolyl]methyl]thio]propionamide
A6 = 3-[[2-[(Diaminomethylene)amino]-4-thiazolyl]methyl]sulphinyl-$N^2$-sulphamoylpropionamide maleate

EXAMPLE 5

Preparation of Coated Famotidine Particles

A. Rotogranulation.

5.2 kg of Famotidine, 2.4 kg. of Hydroxypropyl Methylcellulose (grade Methocel E5) and 32.4 kg. of Lactose are combined in a rotor granulator bowl. For rotor granulation water (approx. 10 kg.) is sprayed at a rotor speed of 500 RPM. The rotogranulated particles are dried to a temperature of 30°-35° C. after decreasing rotor speed to 250 RPM.

B. Particle coating.

The particles produced in Example 5A are coated in a Wurster coating apparatus. The polymer coating solution consists of a 10% by weight solution of cellulose acetate 398-10 (39.8% acetyl content; 10 seconds viscosity) and Hydroxypropylcellulose (Klucel EF) where the ratio of CA to HPC is 70/30. The solvent used is an 80/20 mixture of acetone/methanol. 10% by weight of the polymer is applied to the particles. The product temperature is maintained at 41° C. during the coating step.

EXAMPLE 6

Preparation of Chewable Tablets

The following ingredients are dry blended and compressed by standard procedures into round chewable tablets each weighing approx. 1172 mg. Each tablet contains 10 mg. of famotidine (from coated particles prepared in accordance with the procedure of Example 5A) and 500 mg. of sucralfate as active ingredients.

| Ingredients | mg./Tablet |
|---|---|
| Famotidine Coated Particles | 90.4 |
| Sucralfate Granules[1] | 560 |
| Directly Compressible Sugar | 500 |
| Artificial Sweetener | 2.0 |
| Magnesium Stearate | 15.0 |
| Flavor | 5.0 |
| Total Tablet Weight | 1172.4 |

[1]The Sucralfate granules contain 500 mg. of active ingredients, 50 mg. of pregelatinized starch and 10 mg. of sodium carboxymethyl cellulose as binders. The granules are prepared in a high shear granulator and dried in a fluid bed drier.

EXAMPLE 7

Preparation of Swallowable Tablets

The ingredients listed below are dry blended and compressed by standard procedures into round or caplet shaped polymer coated swallowable tablets each weighing approx. 687 mg. Each tablet contains 10 mg. of famotidine (from coated particles prepared in accordance with the procedure of Example 5A) and 500 mg. of sucralfate as active ingredients.

| Ingredients | mg./Tablet |
|---|---|
| Famotidine Coated Particles | 90.4 |
| Sucralfate Granules[1] | 560 |
| Avicel PH101 | 10.0 |
| Magnesium Stearate | 4.0 |
| Polymer Coating (HPMC/HPC) | 22.33 |
| Total Tablet Weight | 686.73 |

[1]The Sucralfate granules contain 500 mg. of active ingredients, 50 mg. of pregelatinized starch and 10 mg. of sodium carboxymethyl cellulose as binders. The granules are prepared in a high shear granulator and dried in a fluid bed drier.

What is claimed is:

1. A stabilized solid oral dosage form for treatment of gastric disorders, which dosage form comprises famotidine and sucralfate, the famotidine being provided with a barrier layer which prevents interaction between the famotidine and the sucralfate in the dosage form.

2. The dosage form of claim 1, wherein the famotidine is in granulate form and the barrier layer comprises a layer which substantially coats each discrete granule of famotidine.

3. The dosage form of claim 1, wherein the barrier layer is a film forming polymer.

4. The dosage form of claim 2, wherein the barrier layer is a film forming polymer.

5. The dosage form of claim 1, wherein the film-forming polymer is a pharmaceutically acceptable film forming polymer selected from the group consisting of cellulose derivatives, polyvinyl pyrrolidone, polyvinyl alcohol, polyvinyl acetate, polyethylene glycols, copolymers of styrene and acrylate, copolymers of acrylic acid and methacrylic acid, copolymers of methacrylic acid and ethylacrylate, copolymers of methyl methacrylate and methacrylate, copolymers of acrylic acid and tertiary amino alkyl methacrylate, copolymers of methacrylate and tertiary amino alkyl methacrylate, copolymers of ethylacrylate methyl methacrylate and quaternary amino alkyl methacrylate and combinations of two or more thereof.

6. The dosage form of claim 2, wherein the film-forming polymer is a pharmaceutically acceptable film forming polymer selected from the group consisting of cellulose derivatives, polyvinyl pyrrolidone, polyvinyl alcohol, polyvinyl acetate, polyethylene glycols, copolymers of styrene and acrylate, copolymers of acrylic acid and methacrylic acid, copolymers of methacrylic acid and ethylacrylate, copolymers of methyl methacrylate and methacrylate, copolymers of acrylic acid and tertiary amino alkyl methacrylate, copolymers of methacrylate and tertiary amino alkyl methacrylate, copolymers of ethylacrylate methyl methacrylate and quaternary amino alkyl methacrylate and combinations of two or more thereof.

7. The dosage form of claim 5, wherein the film forming polymer is a blend of hydroxypropylcellulose and cellulose acetate.

8. The dosage form of claim 6, wherein the film forming polymer is a blend of hydroxypropylcellulose and cellulose acetate.

9. The dosage form of claim 1 in the form of a tablet.

10. The dosage form of claim 2 in the form of a tablet.

11. The dosage form of claim 3 in the form of a tablet.

12. The dosage form of claim 4 in the form of a tablet.

13. The dosage form of claim 5 in the form of a tablet.

14. The dosage form of claim 6 in the form of a tablet.

15. The dosage form of claim 1 wherein the weight ratio of famotidine to sucralfate present in the dosage form is between 1:10 and 1:75.

16. The dosage form of claim 1 which further contains at least one excipient.

17. The dosage form of claim 1 comprising a bilayer tablet containing a famotidine layer and a sucralfate layer wherein said layers are separated by an intermediate barrier layer.

18. A stabilized solid oral dosage form for treatment of gastric disorders, which dosage form consists essentially of famotidine and sucralfate, the famotidine being provided with a barrier layer which prevents interaction between the famotidine and the sucralfate in the dosage form.

* * * * *